(12) United States Patent
Shen et al.

(10) Patent No.: US 12,025,436 B2
(45) Date of Patent: Jul. 2, 2024

(54) STRAIN GAUGE, FORCE SENSOR AND INTERVENTIONAL MEDICAL CATHETER

(71) Applicant: SHANGHAI MICROPORT EP MEDTECH CO., LTD., Shanghai (CN)

(72) Inventors: Lei Shen, Shanghai (CN); Hui Wang, Shanghai (CN); Ziyan Zhou, Shanghai (CN); Bo Liang, Shanghai (CN)

(73) Assignee: SHANGHAI MICROPORT EP MEDTECH CO., LTD., Shanghai (CN)

( * ) Notice: Subject to any disclaimer, the term of this patent is extended or adjusted under 35 U.S.C. 154(b) by 273 days.

(21) Appl. No.: 17/778,560

(22) PCT Filed: Sep. 11, 2020

(86) PCT No.: PCT/CN2020/114840
§ 371 (c)(1),
(2) Date: May 20, 2022

(87) PCT Pub. No.: WO2021/098351
PCT Pub. Date: May 27, 2021

(65) Prior Publication Data
US 2022/0412716 A1 Dec. 29, 2022

(30) Foreign Application Priority Data

Nov. 21, 2019 (CN) .......................... 201911150588.8

(51) Int. Cl.
*A61M 25/00* (2006.01)
*A61M 39/00* (2006.01)
(Continued)

(52) U.S. Cl.
CPC ............... *G01B 7/16* (2013.01); *A61M 25/00* (2013.01); *G01L 1/2218* (2013.01); *A61M 2025/0002* (2013.01)

(58) Field of Classification Search
CPC . G01B 7/16; A61M 2025/0002; A61M 25/00; G01L 1/2218; G01L 1/2287
See application file for complete search history.

(56) References Cited

U.S. PATENT DOCUMENTS

2010/0063478 A1\* 3/2010 Selkee ............... A61B 18/1492
604/524
2020/0100859 A1\* 4/2020 Shen ...................... A61B 90/06

FOREIGN PATENT DOCUMENTS

CN          1776385 A       5/2006
CN        105180793 A   *  12/2015
(Continued)

*Primary Examiner* — Andre J Allen
(74) *Attorney, Agent, or Firm* — MUNCY, GEISSLER, OLDS & LOWE, P.C.

(57) ABSTRACT

A strain gauge includes: a substrate; a transverse sensitive grid arranged on the substrate; and at least two non-transverse sensitive grids arranged on the substrate so as to be located on opposite sides of the transverse sensitive grid both electrically connected to the transverse sensitive grid. The two non-transverse sensitive grids are connected to each other by a connection and share a common ground lead and a common ground interface. One end of the ground lead is connected to the connection at the middle thereof. The other end of the ground lead is connected to the ground interface. The two non-transverse sensitive grids have equal resistances and are connected to ends of two respective non-ground leads having equal resistances. The other ends of the two non-ground leads are connected to two respective non-ground interfaces.

14 Claims, 5 Drawing Sheets

(51) Int. Cl.
*G01B 7/16* (2006.01)
*G01L 1/22* (2006.01)

(56) References Cited

FOREIGN PATENT DOCUMENTS

| | | |
|---|---|---|
| CN | 105241371 A | 1/2016 |
| CN | 109141697 A | 1/2019 |
| CN | 209069200 U | 7/2019 |
| CN | 210774452 U | 6/2020 |
| DE | 19826411 A1 * 12/1999 | ........... G01L 1/2287 |
| JP | H08166300 A | 6/1996 |
| RU | 138044 U1 | 2/2014 |
| RU | 2506965 C2 | 2/2014 |
| SU | 289808 A1 | 1/1971 |
| WO | WO-2018/228290 A1 | 12/2018 |

* cited by examiner

STRAIN GAUGE, FORCE SENSOR AND INTERVENTIONAL MEDICAL CATHETER

TECHNICAL FIELD

The present invention relates to the technical field of medical instruments and, more specifically, to a strain gauge, a force sensor and an interventional medical catheter.

BACKGROUND

A strain gauge is generally constructed by attaching a metallic sensitive grid onto a plastic membrane substrate. The metallic sensitive grid is formed by a thin conductive wire arranged into a zigzag pattern of parallel lines. When the strain gauge is stretched, the sensitive grid will become narrower and longer, which increases its electrical resistance. When the strain gauge is compressed, the sensitive grid will broaden and shorten, which decreases its electrical resistance. An interventional catheter is usually provided, at its distal end, with a force sensor for detecting how the catheter contacts tissue in the body. Strain gauges can be used to produce such sensors. More specifically, a strain gauge may be attached to a circumferential wall of an elastic tube arranged in the vicinity of an electrode at the distal end. When the electrode comes into contact with tissue in the body, the catheter may deform and in turn cause deformation of the elastic tube, which may elongate or shorten the sensitive grid of the strain gauge, leading to a change in its resistance. In this way, force measurement is made possible.

At present, commonly used commercially available resistive strain gauges typically have only one longitudinally arranged sensitive grid consisting of a wire with a relatively large circumferential surface area. The applicant has ever proposed a compact strain gauge composed of a substrate and a plurality of longitudinal sensitive grids arranged on the substrate. However, during practical use of this strain gauge, the applicant has found that, it has to be pre-heated for a period of time (about from 5 to 6 minutes) before it attains a stable condition suitable for pressure measurement. This may extend a surgical procedure and cause inconvenience of use.

SUMMARY OF THE INVENTION

In view of the above-described shortcomings of the prior art, it is an object of the present invention to provide a strain gauge, a force sensor and an interventional medical catheter. The strain gauge can be stabilized very rapidly, overcoming the problem of inconvenient use associated with the existing strain gauge caused by a required period of time for pre-heating.

To this end, the strain gauge provided in the present invention comprises:

a substrate;

a transverse sensitive grid arranged on the substrate; and at least two non-transverse sensitive grids both arranged on the substrate so as to be located on opposite sides of the transverse sensitive grid and both electrically connected to the transverse sensitive grid, wherein the two non-transverse sensitive grids are connected to each other by a transverse connection and share a common ground lead and a common ground interface, one end of the ground lead connected to the transverse connection at the middle thereof, the other end of the ground lead connected to the ground interface, the two non-transverse sensitive grids having equal resistances and connected to ends of two respective non-ground leads having equal resistances, the other ends of the two non-ground leads connected to two respective non-ground interfaces.

Optionally, in the strain gauge, the substrate may define a first direction and a second direction, wherein the first direction is one of a lengthwise direction and a widthwise direction of the substrate, and the second direction is the other of the lengthwise and widthwise directions of the substrate.

Optionally, in the strain gauge, the two non-transverse sensitive grids may be arranged in symmetry and each long a direction inclined from the first direction at a predetermined angle, with the transverse sensitive grid being arranged along the second direction.

Optionally, in the strain gauge, the two non-transverse sensitive grids may be longitudinal sensitive grids which are arranged side by side and aligned with each other along the first direction, with the transverse sensitive grid being arranged along the second direction, wherein grid widths of the longitudinal sensitive grids are aligned with a grid length of the transverse sensitive grid, or grid lengths of the longitudinal sensitive grids are aligned with a grid width of the transverse sensitive grid.

Optionally, in the strain gauge, a grid width of each of the sensitive grids may be equal to a grid length thereof, wherein the grid-like structures in the sensitive grids are all identical.

Optionally, in the strain gauge, the transverse sensitive grid may be electrically connected to the two non-transverse sensitive grids through the transverse connection, wherein the transverse sensitive grid and the two non-transverse sensitive grids share the common ground lead and the common ground interface.

Optionally, in the strain gauge, the transverse sensitive grid may comprise transverse wire segments, which are connected to the transverse connection at a location close to the middle of the transverse connection.

Optionally, in the strain gauge, the ground lead may comprise a transverse segment and a longitudinal segment, the transverse segment connected to the transverse connection at the middle thereof, the longitudinal segment connected to the transverse segment at one end and to the ground interface at the other end.

Optionally, in the strain gauge, the transverse sensitive grid may comprise transverse wire segments arranged in parallel to the transverse segment and perpendicular to the longitudinal segment.

Optionally, in the strain gauge, the two non-transverse sensitive grids may include a first non-transverse sensitive grid and a second non-transverse sensitive grid, which are connected to a first non-ground lead and a second non-ground lead, respectively, wherein one end of the transverse sensitive grid is connected to the transverse connection, and the other end of the transverse sensitive grid is connected to a third non-ground lead, wherein the first, second and third non-ground leads have equal resistances, and wherein the third non-ground lead is connected to a third non-ground interface.

The force sensor provided in the present invention comprises an elastomer and strain gauges as defined in any of the above paragraphs, which are provided on the elastomer.

Optionally, in the force sensor, the elastomer may be provided therein with a plurality of through-slots extending circumferentially around the elastomer, each of which is provided at each end thereof with an axial slot extending along an axis of the elastomer.

Optionally, in the force sensor, the axial slots may each have a length that is not less than the grid width or grid length of each sensitive grid in each strain gauge, or not less than a width of each sensitive grid along the axial of the elastomer.

The interventional medical catheter provided in the present invention comprises a distal catheter end, at which a force sensor as defined in any of the above paragraphs is provided.

Compared to the prior art, the strain gauge provided in the present invention includes a substrate, one transverse sensitive grid arranged on the substrate, and two non-transverse sensitive grids both arranged on the substrate so as to be located on opposite sides of the transverse sensitive grid and both electrically connected to the transverse sensitive grid, wherein the two non-transverse sensitive grids are connected to each other by a transverse connection and share a common ground lead and a common ground interface, wherein one end of the ground lead is connected to the transverse connection at the middle thereof, and the other end of the ground lead is connected to the ground interface, wherein the two non-transverse sensitive grids have equal resistances and are connected to ends of two respective non-ground leads having equal resistances, and wherein the other ends of the two non-ground leads are connected to two respective non-ground interfaces. This design allows higher accuracy, faster attainment of a stable condition when connected in a circuit and enhanced interference rejection performance of the strain gauge. According to the present invention, through employing the strain gauge in the force sensor and the interventional catheter, the period of time for preheating the catheter in the human body can be effectively shortened, and the complexity and risk of a surgical procedure to be performed by a physician and a patient's suffering can be reduced.

BRIEF DESCRIPTION OF THE DRAWINGS

In the drawings, identical reference numbers identify similar elements or actions. The sizes and relative positions of the elements in the drawings are not necessarily drawn to scale. For example, the forms of the various elements and angles are not necessarily drawn to scale, and some of these elements are enlarged and located arbitrarily to improve the understanding of the drawing. In addition, the particular forms of the elements as drawn do not intend to convey any information concerning the real shape of the particular elements and only have been selected to facilitate its recognition in the drawings, wherein.

DETAILED DESCRIPTION

Objects, aspects and advantages of the present invention will become more clear and apparent from the following more detailed description of embodiments thereof, which is to be read in connection with the accompanying drawings. It is to be understood that the specific embodiments described herein are merely intended to explain the invention, rather than limit the invention.

As used hereinabove, the terms "proximal" and "distal" describe relative orientations, relative positions and directions between elements or actions, as viewed by an operating physician. Without wishing to be limiting, a "proximal end" usually refers to an end closer to the doctor, and a "distal end" usually refers to an end that enters the patient first, during normal operation. The terms "axial" and "circumferential" refer to directions respectively along an axis and a circumferential surface of an elastomer.

Figure 1:
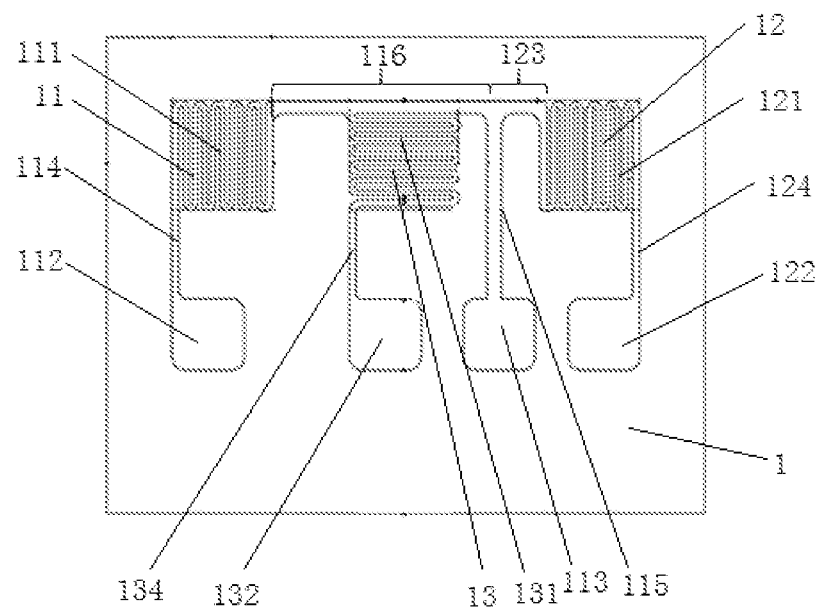
FIG. 1 is a schematic diagram illustrating the structure of an existing strain gauge according to an embodiment of prior art.
Figure 2:
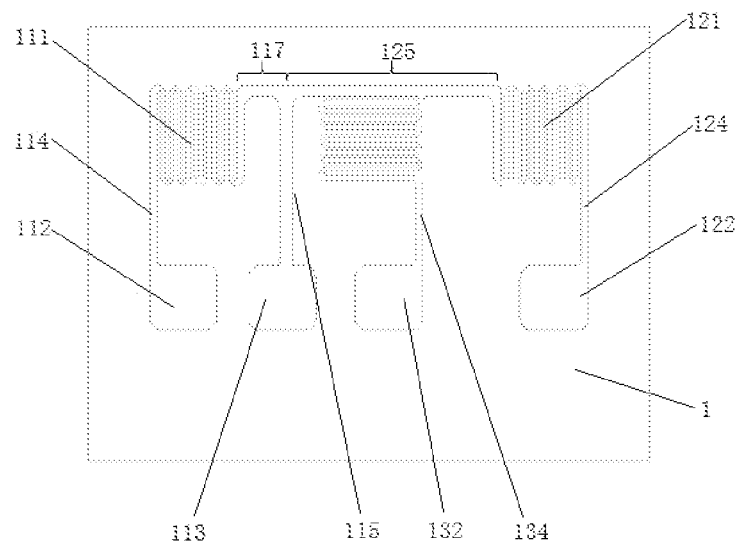
FIG. 2 is a schematic diagram illustrating the structure of the existing strain gauge according to another embodiment of prior art.
Figure 3:
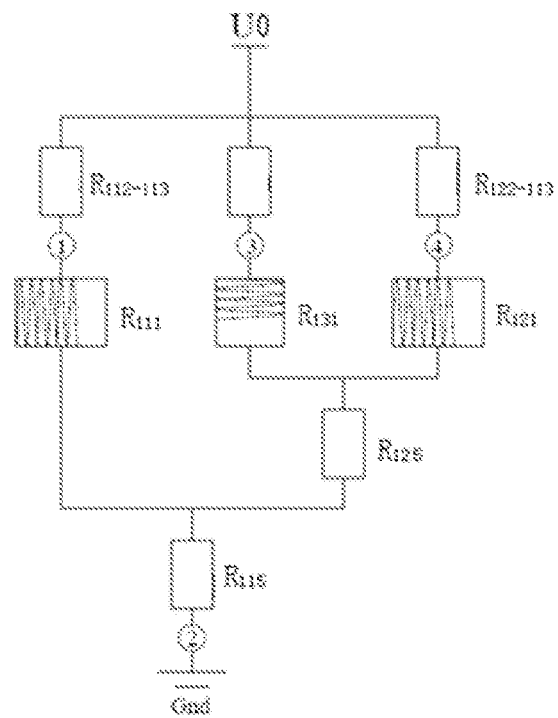
FIG. 3 is a diagram showing a half Wheatstone bridge circuit of the strain gauge of FIG. 2.

FIGS. 1 to 3 are schematic diagrams illustrating the structure of an existing strain gauge. The strain gauge includes three sensitive grids: two longitudinal sensitive grids (the first longitudinal sensitive grid 11 and the second longitudinal sensitive grid 12) and one transverse sensitive grid (the first transverse sensitive grid 13). The three sensitive grids are electrically interconnected by connections.

Specifically, the first longitudinal sensitive grid 11 includes a first grid-like structure 111, a first non-ground interface 112, a ground interface 113, a ground lead 115 connected to the ground interface 113 (this ground lead is a wire connected to one end of the first grid-like structure 111 by a first connection 116/117) and a first non-ground lead 114 connected to the first non-ground interface 112 (the first non-ground lead 114 is another wire connected to the other end of the first grid-like structure 111).

The second longitudinal sensitive grid 12 includes a second grid-like structure 121, a second non-ground interface 122, the ground interface 113 shared with the first longitudinal sensitive grid 11, the ground lead 115 connected to the ground interface 113 (the ground lead is connected to one end of the second grid-like structure 121 by a second connection 123/125) and a second non-ground lead 124 connected to the second non-ground interface 122 (the second non-ground lead 124 is connected to the other end of the second grid-like structure 121).

The first transverse sensitive grid 13 includes a third grid-like structure 131, a third non-ground interface 132, the ground interface 113 shared with both the first longitudinal sensitive grid 11 and the second longitudinal sensitive grid 12, the ground lead 115 connected to the ground interface 113 and a third non-ground lead 134 connected to the third non-ground interface 132. The ground lead 115 is connected to one end of the third grid-like structure 131 by part of the first connection 116 (as shown in FIG. 1) or by part of the second connection 125 (as shown in FIG. 2), and the third non-ground lead 134 is connected to the other end of the third grid-like structure 131.

Studies found that, during practical use, the above strain gauge requires post-calibration of the sensed values and has to be preheated for a period of time before it reaches a stable condition that makes it available for use. These create inconvenience of use. In order to overcome this, the applicant has conducted extensive research and found that the above problems are related to the location where the ground lead extends from.

As can be seen from the figures, in the existing strain gauge, the ground lead 115 that is connected to the ground interface 113 extends from the middle between the second longitudinal sensitive grid 12 and the first transverse sensitive grid 13 (as shown in FIG. 1), or from the middle between the first longitudinal sensitive grid 11 and the first transverse sensitive grid 13 (as shown in FIG. 2). This may lead to unequal resistances between the first non-ground interface 112 and the ground interface 113 and between the second non-ground interface 122 and the ground interface 113, which cause the above problem.

Specifically, as shown in FIG. 2, the resistance $R_{112\text{-}113}$ between the first non-ground interface 112 and the ground interface 113 is equal to a resistance $R_{111}$ of the first grid-like structure plus a resistance $R_{115}$ of the ground lead plus a resistance $R_{114}$ of the first non-ground lead and plus a resistance $R_{117}$ of the first connection, and the resistance $R_{122\text{-}113}$ between the second non-ground interface 122 and the ground interface 113 is equal to a resistance $R_{121}$ of the second grid-like structure plus the resistance $R_{115}$ of the ground lead plus a resistance $R_{124}$ of the second non-ground lead plus a resistance $R_{125}$ of the second connection. Since the ground interface 113 is a shared interface, if it is assumed that the resistance $R_{114}$ of the first non-ground lead is equal to the resistance $R_{124}$ of the second non-ground lead, in order to ensure that $R_{112\text{-}113}$ is equal to $R_{122\text{-}113}$, the sum of the resistance $R_{111}$ of the first grid-like structure and the resistance $R_{117}$ of the first connection should be equal to the sum of the resistance $R_{121}$ of the second grid-like structure and the resistance $R_{125}$ of the second connection. As the resistance $R_{117}$ of the first connection is apparently lower than the resistance $R_{125}$ of the second connection, the resistances of the two longitudinal strain-sensitive grids satisfy $R_{111} > R_{121}$, requiring the two longitudinal sensitive grids to have different wire sizes. As shown in FIG. 3, the wires and connections in the existing strain gauge form a Wheatstone bridge circuit, in which the resistance $R_{125}$ of the second connection is connected in series individually with each of the resistance $R_{121}$ of the second grid-like structure and the resistance $R_{131}$ of the third grid-like structure, and the three are then connected as a whole in parallel with the resistance $R_{111}$ of the first grid-like structure.

Therefore, the existing strain gauge has to be designed with different wire sizes of the two longitudinal sensitive grids or post-calibration of output force values. However, both these options involve a complex design and inadequate accuracy. Additionally, this strain gauge must be preheated for 5 to 6 minutes before it becomes stable and available for measurement. Accordingly, an interventional medical catheter employing the strain gauge would require an extended period of time for preheating after being delivered into the human body. This may impair the use of the strain gauge in the interventional medical catheter, increase the complexity and risk of an operation procedure to be performed by a doctor, and prolong a patient's suffering.

In view of the above problems of the existing strain gauge, the present invention provides a novel strain gauge, which provides higher accuracy, increased stability when connected in a circuit, and improved interference rejection performance, dispenses with the need for post-calibration, and can reach a stable condition in a very short time. When employed in a force sensor or an interventional medical catheter, the strain gauge of the present invention can effectively shorten the required period of time for preheating the catheter in the human body, reduce the complexity and risk of a surgical procedure to be performed by a doctor, and alleviate a patient's suffering.

As shown in FIGS. 4 to 7, the strain gauge provided in the present invention includes: a substrate 1; one transverse sensitive grid 13 arranged on the substrate 1; and two non-transverse sensitive grids both arranged on the substrate 1 so as to be located on opposite sides of the transverse sensitive grid 13 respectively and both electrically connected to the transverse sensitive grid 13.

The two non-transverse sensitive grids are connected to each other by the transverse connection 210 and share a common ground lead 115 and a common ground interface 113. One end of the ground lead 115 is connected to the connection 210 at the middle thereof, and the other end of the ground lead 115 is connected to the ground interface 113. The two non-transverse sensitive grids have equal resistances and are connected to ends of two non-ground leads having equal resistances, respectively. The other ends of the two non-ground leads are connected to two non-ground interfaces, respectively.

In the present embodiment, the substrate 1 defines a first direction and a second direction. The first direction is one of a lengthwise direction and a widthwise direction of the substrate, and the second direction is the other of the lengthwise and widthwise directions.

Preferably, the connection 210 includes a third connection 211 and a fourth connection 212, which are joined to and electrically connected with each other. The ground lead 115 extends from the junction of the third connection 211 and the fourth connection 212 (i.e., the middle of the connection 210). The third connection 211 has a length that is equal to a length of the fourth connection 212. The transverse sensitive grid 13 is electrically connected by the transverse connection 210 to, and shares the common ground lead 115 and the common ground interface 113 with, both the two non-transverse sensitive grids. In accordance with this embodiment of the present invention, sharing the common ground interface 113 among the three sensitive grids and connecting the ground lead 115 to the middle of the connection 210 ensure that a resistance $R_{112\text{-}113}$ between the first non-ground interface 112 and the ground interface 113 is equal to a resistance $R_{122\text{-}113}$ between the second non-ground interface 122 and the ground interface 113. This imparts increased stability when connected to a circuit and enhanced interference rejection performance to the strain gauge and enables it to attain a stable condition very rapid, significantly shortening the required period of time for preheating. Moreover, the strain gauge is required to have fewer ground interfaces for connection to a ground interface of an external power supply, leading to shrinkage of the strain gauge and hence of a force sensor or interventional medical catheter employing the strain gauge. This helps reduce interventional cost and the risk of patient infection, resulting an increased success rate of interventional treatment. Preferably, according to the present invention, both the length and width of the substrate 1 are not more than 2.0 mm in order to facilitate the strain gauge's attachment to and use with an interventional medical catheter and enhance its adaptability.

In this embodiment, the ground lead 115 includes a transverse segment 1151 and a longitudinal segment 1152.

The transverse segment 1151 is connected to the connection 210 at the middle thereof, and the longitudinal segment 1152 is connected to the transverse segment 1151 at one end and to the ground interface 113 at the other end. Specifically, the transverse segment 1151 is arranged in parallel to transverse wire segments in the transverse sensitive grid 13, while the longitudinal segment 1152 is arranged to be perpendicular to the transverse wire segments in the transverse sensitive grid 13. This design avoids dislocation of the transverse sensitive grid 13 and retains it around a center of the strain gauge. In this way, the various interfaces of the strain gauge are spaced apart by proper distances, which avoid short-circuiting during welding.

Additionally, in this embodiment, the transverse wire segments in the transverse sensitive grid 13 are connected to the connection 210 in the vicinity of the middle thereof. This allows the transverse sensitive grid 13 to become stable at a same time as that of the non-transverse sensitive grids, thus additionally improving the strain gauge's performance during use.

Figure 4:
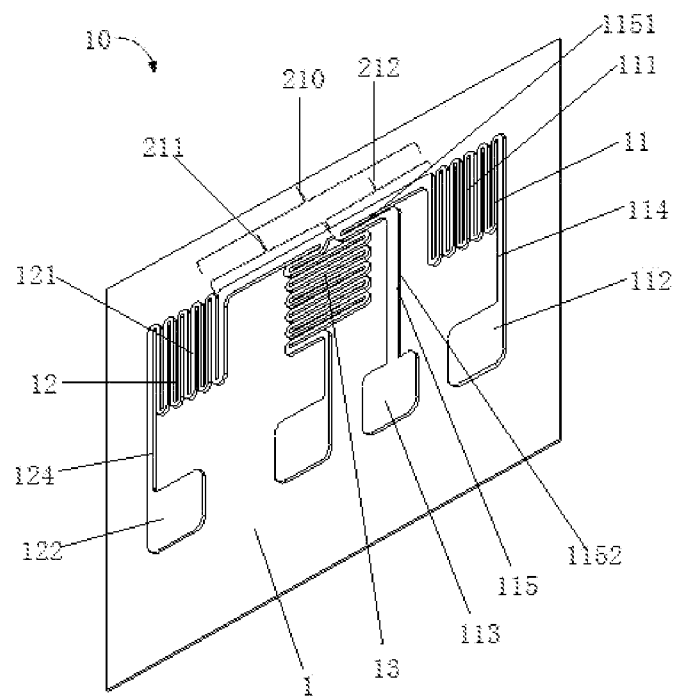
FIG. 4 shows an isometric view of a strain gauge according to an embodiment of the present invention.
Figure 5:
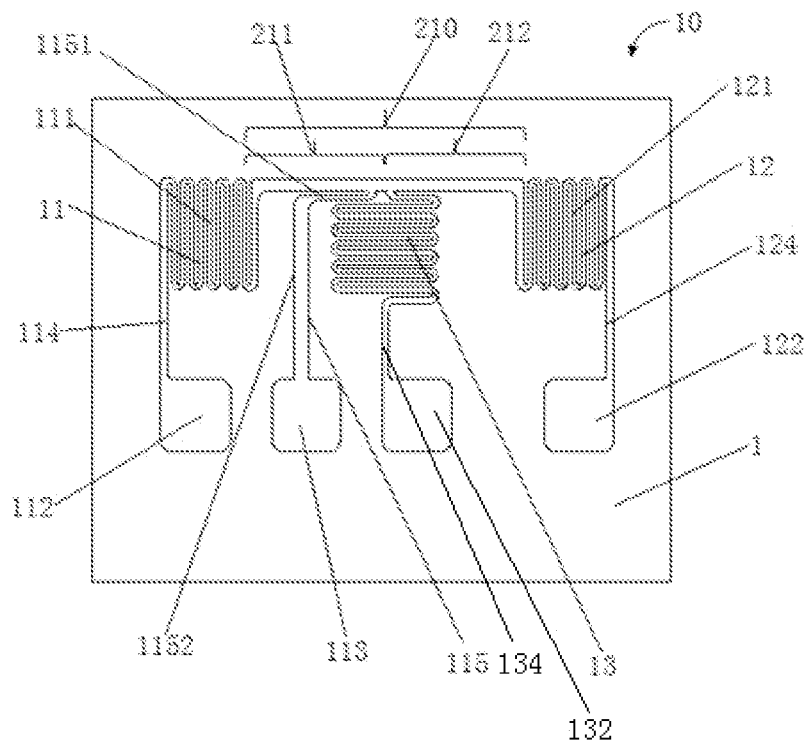
FIG. 5 shows a bottom view of the strain gauge of FIG. 4.

As shown in FIGS. 4 to 5, in an embodiment of the present invention, the two non-transverse sensitive grids are longitudinal sensitive grids (i.e., a first longitudinal sensitive grid 11 and a second longitudinal sensitive grid 12). The first longitudinal sensitive grid 11 and the second longitudinal sensitive grid 12 may be implemented as being arranged side by side and aligned with each other along the first direction (i.e., longitudinal wire segments therein extend in the first direction), with the transverse sensitive grid 13 being disposed therebetween. The transverse sensitive grid 13 is arranged along the second direction (i.e., the transverse wire segments therein extend in this direction). Grid widths of the two longitudinal sensitive grids 11, 12 may be aligned with a grid length of the transverse sensitive grid 13. Alternatively, grid lengths of the two longitudinal sensitive grids 11, 12 may be aligned with a grid width of the transverse sensitive grid 13.

In this embodiment, a resistance $R_{112\text{-}113}$ between the first non-ground interface 112 and the ground interface 113 of the strain gauge is equal to a resistance $R_{111}$ of the first grid-like structure plus a resistance $R_{115}$ of the ground lead plus a resistance $R_{114}$ of the first non-ground lead plus a resistance $R_{211}$ of the third connection, and a resistance $R_{122\text{-}113}$ between the second non-ground interface 122 and the ground interface 113 is equal to a resistance $R_{121}$ of the second grid-like structure plus the resistance $R_{115}$ of the ground lead plus a resistance $R_{124}$ of the second non-ground lead plus a resistance $R_{212}$ of the fourth connection. The applicant has found from research that the resistances of the connections depend on the location where the ground lead extends from. According to embodiments of the present invention, connecting the ground lead 115 to the middle of the connection 210 can ensure that the left and right connections, i.e., the third connection 211 and the fourth connection 212 have the same length and resistance. In this way, when the wire resistance of the first longitudinal strain sensitive grid 11 is equal to that of the second longitudinal strain sensitive grid 12, i.e., the resistance $R_{111}$ of the first grid-like structure is equal to the resistance $R_{121}$ of the second grid-like structure, the resistance $R_{112\text{-}113}$ between the first non-ground interface 112 and the ground interface 113 will be equal to the resistance $R_{122\text{-}113}$ between the second non-ground interface 122 and the ground interface 113. This can result in increased accuracy, high stability when connected in a circuit, a shorter period of time for preheating taken to attain a stable condition (in only 2-3 seconds in the present embodiment, as compared to in 5-6 minutes for the existing strain gauge) and enhanced interference rejection performance of the strain gauge.

Preferably, in this embodiment, the grid width of each sensitive grid in the strain gauge is equal to the grid length thereof, and the grid-like structures of the sensitive grids are all identical. In addition, one end of the transverse sensitive grid 13 is connected to the connection 210, and the other end of the transverse sensitive grid 13 is connected to the third non-ground lead 134. The third non-ground lead 134, the first non-ground lead 114 and the second non-ground lead 124 have equal resistances, and the third non-ground lead 134 is connected to the third non-ground interface 132. This enables the strain gauge to have a more compact and more stable structure.

Figure 6:
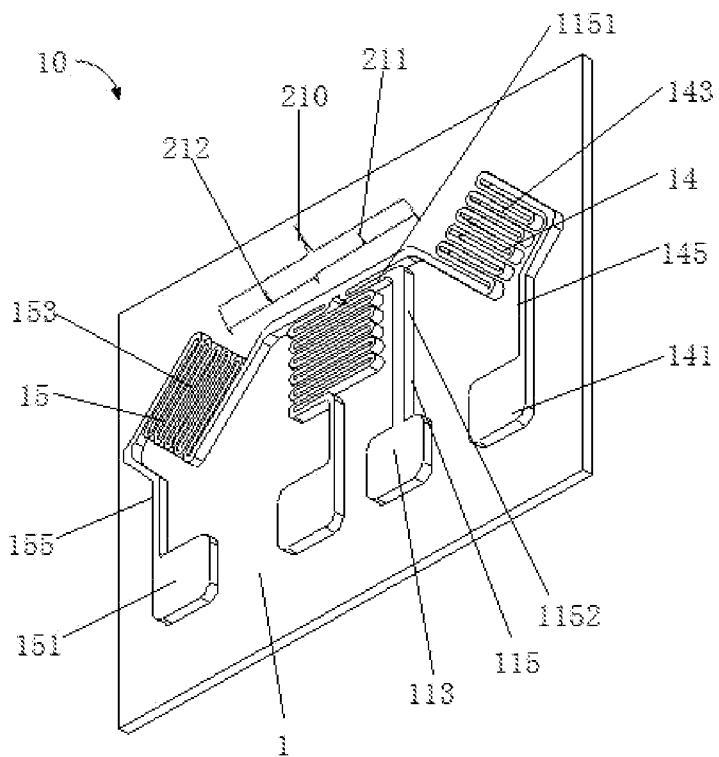
FIG. 6 shows an isometric view of a strain gauge according to another embodiment of the present invention.
Figure 7:
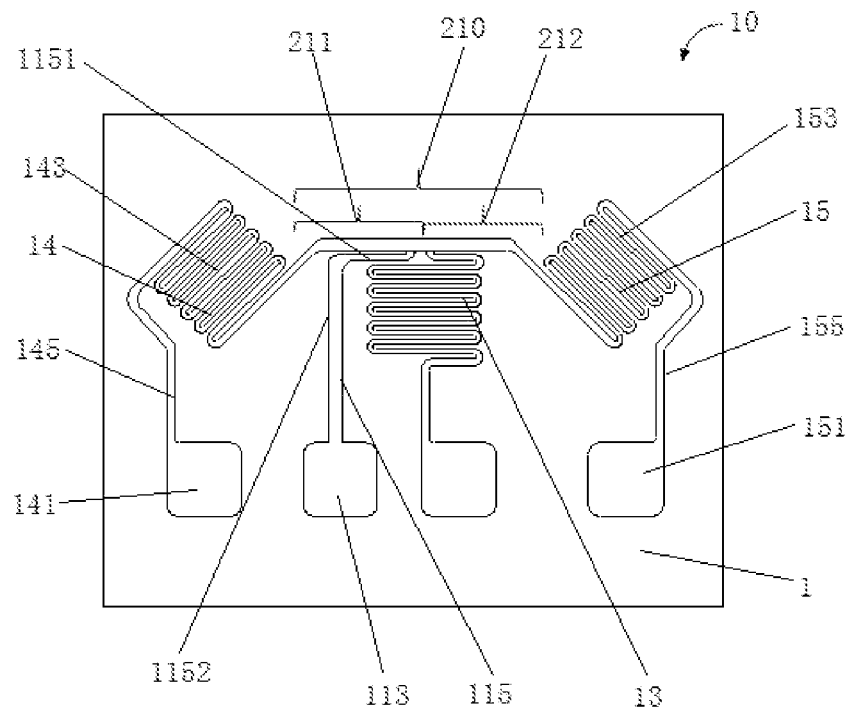
FIG. 7 shows a top view of the strain gauge of FIG. 6.

Considering that, in some cases, strain may occur not along the direction of a center axis of the strain gauge but along a direction inclined therefrom at an angle of even possibly up to 90 degrees (e.g., under the action of a force along a radial direction (i.e., a transverse force)), as shown in FIGS. 6 to 7, in another embodiment of the present invention, the two non-transverse sensitive grids (i.e., the first non-transverse sensitive grid 14 and the second non-transverse sensitive grid 15) are arranged in symmetry and oriented at a predetermined angle with respect to the first direction, with the transverse sensitive grid 13 being arranged along the second direction. This arrangement enables both axial and transverse strain measurement of the strain gauge, expanding its scope of application.

Preferably, in this embodiment, in addition to the above described structural details of the strain gauge, the wires in the left and right non-transverse sensitive grids may be deflected by an angle in order to address biaxial stress measurement and analysis in cases with the directions of the principal axes remaining unknown. Preferably, the wires are deflected by 45° (i.e., forming an angle of 45° with the first direction). This enables the strain gauge to address the measurement of unknown stresses as many as possible and to monitor forces from various directions, thereby providing a doctor with more accurate stress direction information.

In this embodiment, a resistance $R_{141\text{-}113}$ between the non-ground interface 141 of the first non-transverse sensitive grid 14 and the ground interface 113 is equal to a resistance $R_{143}$ of the grid-like structure of the first non-transverse sensitive grid plus the resistance $R_{115}$ of the ground lead plus a resistance $R_{145}$ of the non-ground lead of the first non-transverse sensitive grid plus the resistance $R_{211}$ of the third connection, and a resistance $R_{151\text{-}113}$ between the non-ground interface 151 of the second non-transverse sensitive grid 15 and the ground interface 113 is equal to a resistance $R_{153}$ of the grid-like structure of the second non-transverse sensitive grid plus the resistance $R_{115}$ of the ground lead plus a resistance $R_{155}$ of the non-ground lead of the second non-transverse sensitive grid plus the resistance $R_{212}$ of the fourth connection.

In this embodiment, the ground lead 115 of the ground interface 113 also extends from the middle of the connection 210, allowing the left and right connections, i.e., the third connection 211 and the fourth connection 212, to have the same length and resistance. As such, the resistance $R_{141\text{-}113}$ between the first non-ground interface 141 and the ground interface 113 is equal to the resistance $R_{151\text{-}113}$ between the second non-ground interface 151 and the ground interface 113. This allows increased accuracy, a shorter period of time for preheating and enhanced stability when connected in a circuit of the strain gauge.

In other embodiments, a plurality of, e.g., 4 or 6, pairs of non-transverse sensitive grids may be arranged on the substrate. The non-transverse sensitive grids in each pair may be arranged in symmetry with respect to the transverse sensitive grid so that the two non-transverse sensitive grids on opposite sides of the transverse sensitive grid are spaced apart therefrom by equal distances and have same resistances. The non-transverse sensitive grids are connected to the transverse sensitive grid by transverse connections and share a common ground lead and a common ground interface with the transverse sensitive grid. In such embodiments, the same technique effects can be obtained, and the present invention is not limited in any sense in this regard.

According to the present invention, the substrate 1 is a semi-rigid substrate. Preferably, the substrate 1 is made of a semi-rigid plastic material. For example, the material of the substrate 1 is one selected from the special polymer materials polyimide (PI) and polyetheretherketone (PEEK), or a combination thereof. More preferably, the substrate 1 is fabricated from a PEEK material, which can impart both excellent rigidity and flexibility to the substrate 1.

Figure 8:
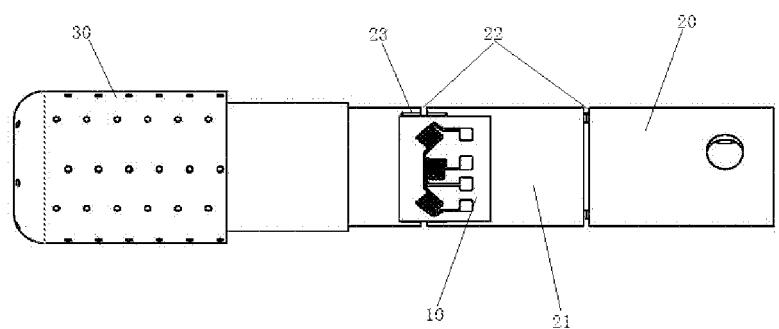
FIG. 8 is a schematic diagram illustrating the structure of a force sensor according to an embodiment of the present invention, which is being attached to an electrode.

The present invention also provides a force sensor 20, which includes, as shown in FIG. 8, an elastomer 21 and strain gauges 10 according to any of the foregoing embodiments. The strain gauges 10 are arranged on the elastomer 21. Preferably, in this embodiment, the elastomer 21 is a cylindrical hollow elastomer.

In this embodiment, the elastomer 21 preferably has at least two circumferentially extending through-slots 22. Preferably, between opposite ends of each through-slot 22, one of the strain gauges 10 is arranged. The through-slots 22 are formed in different circumferential planes and staggered from each other circumferentially (i.e., they are staggered from each other both axially and circumferentially)

In this embodiment, an axial slot 23 is provided at each of the opposite ends of each through-slot 22. Preferably, the axial slot 23 extends along an axis of the elastomer 21 over a length not less than the grid widths or grid lengths of the sensitive grids in the strain gauges, or not less than an axial width of the sensitive grids on the axis of the elastomer 21. Since the grid-like structures of the strain gauges 10 will be subjected to the greatest strain at their portions around the axial slots 23, the above length design allows the axial slots 23 to provide indications that can guide the strain gauges 10 to be attached to the most stressed locations. This enables the strain gauges 10 to output stronger signals, from which better measurements can be obtained.

Figure 9:
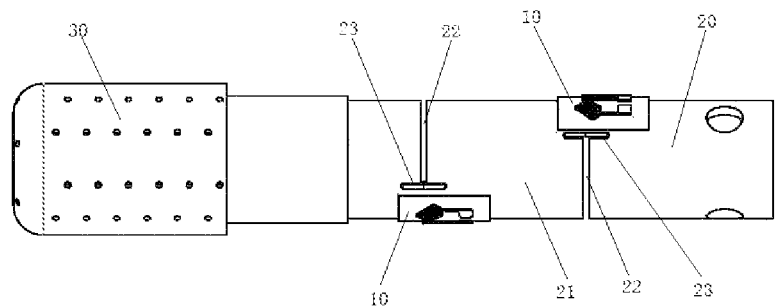
FIG. 9 is an elevation view of an elastomer according to an embodiment of the present invention, on which two strain gauges are evenly distributed.
Figure 10:
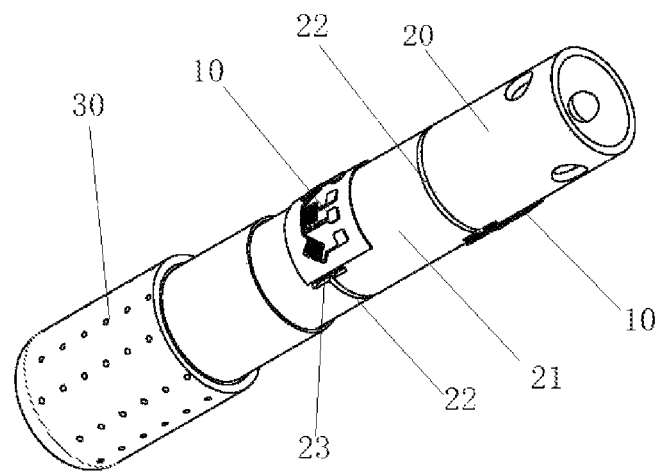
FIG. 10 is a perspective view of an elastomer according to an embodiment of the present invention, on which two strain gauges are evenly distributed.
Figure 11:
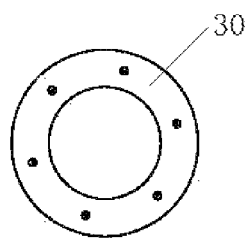
FIG. 11 shows a top view of an electrode disposed at a distal catheter end of an interventional medical catheter according to an embodiment of the present invention.

Specifically, as shown in FIGS. 9 to 10, in this embodiment, the force sensor includes an elastomer 21 and at least two strain gauges 10, which are provided on an external surface of the elastomer 21 in order to measure axial and circumferential strain at at least two different locations of the elastomer 21. The at least two strain gauges 10 are provided in different circumferential planes and staggered from each other circumferentially Orthographic projections of the two strain gauges 10 on a cross section of the elastomer 21 are preferably evenly distributed around the circumference of the elastomer 21.

In this embodiment, two strain gauges, i.e., a first strain gauge and a second strain gauge, are provided, for example. The first strain gauge includes one substrate, two non-transverse sensitive grids and one transverse sensitive grid. The two non-transverse sensitive grids are arranged in symmetry and each along a direction inclined from the axis of the elastomer at a predetermined angle (preferably of 45°). The transverse sensitive grid between the two non-transverse sensitive grids is arranged along the circumference of the elastomer. The second strain gauge includes another substrate, two longitudinal sensitive grids and one transverse sensitive grid. The two longitudinal sensitive grids are arranged side by side and aligned with each other along the axis of the elastomer. The transverse sensitive grid between the two longitudinal sensitive grids is arranged along the circumference of the elastomer.

In practical implementations, the two strain gauges 10 attached to the elastomer 21 may be two first strain gauges, or two second strain gauges, or a combination of one first strain gauge and one second strain gauge (i.e., the two strain gauges 10 may be identical or not). In this embodiment, the two strain gauges are capable of sensing strain at two different locations of the elastomer 21, ensuring that practical contact force measurement needs can be satisfied. The design with the two strain gauges allows a shorter axial length of the elastomer 21 and hence of an interventional medical catheter employing the force sensor, resulting in cost savings.

The present invention also provides an interventional medical catheter including a distal catheter end where the force sensor 20 according to any of the above embodiments is provided. The interventional medical catheter further includes an electrode 30 attached to the force sensor 20, as shown in FIGS. 8 to 11. In this embodiment, the force sensor 20 includes the above described two strain gauges for sensing strain signals.

In summary, in the strain gauge, force sensor and interventional medical catheter provided in the present invention, the shared ground lead extends from the middle of the connection in the strain gauge, which can ensure that the wires in the left and right strain sensitive grids have the same size and resistance and impart higher stability when connected in a circuit and enhanced interference rejection performance to the strain gauge. Through employing the strain gauge in the force sensor and the interventional catheter, the catheter's required period of time for preheating in the human body can be effectively shortened, and the complexity and risk of an operation procedure to be performed by a doctor and a patient's suffering can be reduced. Further, the compactness of the strain gauge of the present invention allows a shorter length of the elastomer in the force sensor and shrinkage of the interventional medical catheter, resulting in cost savings.

The various technical features of the foregoing embodiments may be combined in any way. Although not all such combinations have been described above for the sake of brevity, any of them is considered to fall within the scope of this specification as long as there is no contradiction between the technical features.

Presented above are merely several embodiments of the present application. Although these embodiments are described with some particularity and in some detail, it should not be construed that they limit the scope of the present application in any sense. Note that various variations and modifications can be made by those of ordinary skill in the art without departing from the concept of the present application. Accordingly, it is intended that all such variations and modifications are embraced within the scope of this application as defined in the appended claims

What is claimed is:

1. A strain gauge, comprising:
   a substrate;
   a transverse sensitive grid, arranged on the substrate; and
   at least two non-transverse sensitive grids, both arranged on the substrate so as to be located on opposite sides of the transverse sensitive grid and both electrically connected to the transverse sensitive grid, wherein the two non-transverse sensitive grids are connected to each other by a transverse connection and share a common ground lead and a common ground interface, one end of the ground lead connected to the transverse connection at a middle thereof, the other end of the ground lead connected to the ground interface, the two non-transverse sensitive grids having equal resistances and connected to ends of two respective non-ground leads having equal resistances, the other ends of the two non-ground leads connected to two respective non-ground interfaces.

2. The strain gauge according to claim 1, wherein the substrate defines a first direction and a second direction, the first direction being one of a lengthwise direction and a widthwise direction of the substrate, the second direction being the other of the lengthwise and widthwise directions of the substrate.

3. The strain gauge according to claim 2, wherein the two non-transverse sensitive grids are arranged in symmetry and each long a direction inclined from the first direction at a predetermined angle, with the transverse sensitive grid being arranged along the second direction.

4. The strain gauge according to claim 2, wherein the two non-transverse sensitive grids are longitudinal sensitive grids which are arranged side by side and aligned with each other along the first direction, with the transverse sensitive grid being arranged along the second direction, and wherein grid widths of the longitudinal sensitive grids are aligned with a grid length of the transverse sensitive grid, or grid lengths of the longitudinal sensitive grids are aligned with a grid width of the transverse sensitive grid.

5. The strain gauge according to claim 1, wherein a grid width of each of the sensitive grids is equal to a grid length thereof, and wherein grid-like structures in the sensitive grids are all identical.

6. The strain gauge according to claim 1, wherein the transverse sensitive grid is electrically connected to the two non-transverse sensitive grids through the transverse connection, and wherein the transverse sensitive grid and the two non-transverse sensitive grids share the common ground lead and the common ground interface.

7. The strain gauge according to claim 6, wherein the transverse sensitive grid comprises transverse wire segments which are connected to the transverse connection at a location close to the middle of the transverse connection.

8. The strain gauge according to claim 1, wherein the ground lead comprises a transverse segment and a longitudinal segment, the transverse segment connected to the transverse connection at the middle thereof, the longitudinal segment connected to the transverse segment at one end and to the ground interface at the other end.

9. The strain gauge according to claim 8, wherein the transverse sensitive grid comprises a transverse wire segment arranged in parallel to the transverse segment and perpendicular to the longitudinal segment.

10. The strain gauge according to claim 1, wherein the two non-transverse sensitive grids include a first non-transverse sensitive grid and a second non-transverse sensitive grid, which are connected to a first non-ground lead and a second non-ground lead, respectively, and wherein one end of the transverse sensitive grid is connected to the transverse connection, and the other end of the transverse sensitive grid is connected to a third non-ground lead, the first, second and third non-ground leads having equal resistances, the third non-ground lead connected to a third non-ground interface.

11. A force sensor, comprising an elastomer and strain gauges as defined in claim 1, wherein the strain gauges are provided on the elastomer.

12. The force sensor according to claim 11, wherein the elastomer is provided therein with a plurality of through-slots extending circumferentially around the elastomer, each of the through-slots provided at each of opposite ends thereof with an axial slot extending along an axis of the elastomer.

13. The force sensor according to claim 12, wherein the axial slots each have a length that is not less than a grid width or grid length of each sensitive grid in each strain gauge, or not less than a width of each sensitive grid along the axial of the elastomer.

14. An interventional medical catheter, comprising a distal catheter end provided thereon with a force sensor as defined in claim 11.

* * * * *